US00PP28406P3

(12) United States Plant Patent
Olesen et al.

(10) Patent No.: US PP28,406 P3
(45) Date of Patent: Sep. 19, 2017

(54) *CLEMATIS* PLANT NAMED 'EVIPO049'

(50) Latin Name: *Clematis viticella*
Varietal Denomination: Evipo049

(71) Applicants: Mogens Nyegaard Olesen, Fredensborg (DK); Raymond J. Evison, Guernsey (GB)

(72) Inventors: Mogens Nyegaard Olesen, Fredensborg (DK); Raymond J. Evison, Guernsey (GB)

(73) Assignee: POULSEN ROSER A/S, Fredensbor (DK)

( * ) Notice: Subject to any disclaimer, the term of this patent is extended or adjusted under 35 U.S.C. 154(b) by 55 days.

(21) Appl. No.: 14/756,247

(22) Filed: Aug. 20, 2015

(65) Prior Publication Data

US 2017/0055416 P1 Feb. 23, 2017

(51) Int. Cl.
*A01H 5/02* (2006.01)

(52) U.S. Cl.
USPC ..... Plt./228

(58) Field of Classification Search
USPC ..... Plt./228
See application file for complete search history.

(56) References Cited

PUBLICATIONS http://poulsenroser.com/media/63344/Clematis-2012-2013_Poulsen-Roser_LR_GBP.pdf; Perfection by Poulsen Clematis Main Varieties 2013.*
UPOV hit on Clematis named 'Evipo049', QZ PBR 43280, published Dec. 15, 2014.*

* cited by examiner

*Primary Examiner* — Anne Grunberg

(57) ABSTRACT

A new *Clematis* plant with a compact growth habit, profuse, near white flowers, and continuous summer flowering. The variety successfully propagates from softwood cuttings and is suitable for cultivation in commercial nursery culture. This new and distinct variety has shown to be uniform and stable in the resulting generations from asexual propagation from vegetative cuttings.

1 Drawing Sheet

Botanical classification:
Genus: *Clematis.*
Species: *viticella.*
Variety denomination: 'Evipo049'.

SUMMARY OF THE CLAIMED PLANT

The present invention constitutes a new and distinct variety of *Clematis* plant which originated from a controlled crossing between the female seed parent, an un-named seedling, and the male pollen parent, an un-named seedling. Both parent varieties are non-patented.

The two parents were crossed during the summer of 2001 and the resulting seeds were planted the following winter in a controlled environment in Guernsey, Channel Islands, United Kingdom. The new variety named 'Evipo049' originated as a single seedling from the stated cross.

The new *clematis* plant may be distinguished from its female seed parent and male pollen parent by the following characteristics. The female seed parent and male pollen parent have pure white flowers, while the new variety has near white flowers.

The objective of the hybridization of this *clematis* plant was to create a new and distinct variety for nursery culture with unique qualities such as:

1. Uniform and abundant near white flowers;
2. Vigorous and compact growth, making the variety suitable for container culture; and
3. Improved disease resistance.

This combination of qualities was lacking in *clematis* plants that were in commercial cultivation and the qualities have been substantially achieved in the new variety.

'Evipo049' was selected by Mogens N. Olesen and Raymond J. Evison in their *clematis* development program in the Channel Islands, United Kingdom in 2002. Asexual reproduction of 'Evipo049' by means of vegetative cuttings and traditional layering was first performed by Mogens N. Olesen and Raymond J. Evison in the nursery during the summer of 2002. This initial and subsequent asexual propagations have demonstrated that the characteristics of 'Evipo049' are true to type and are transmitted from one generation to the next.

BRIEF DESCRIPTION OF THE DRAWING

The accompanying color illustration shows as true as is reasonably possible to obtain in color photographs of this type the typical characteristics of the buds, flowers, leaves, and stems, of 'Evipo049'. Specifically illustrated in the drawing are flowers at various stages of development, flower in parts, leaves, and stems. Plants shown are 2 years of age.

DETAILED DESCRIPTION OF THE VARIETY

The following is a detailed description of 'Evipo049', as observed in its growth throughout the flowering period in Yamhill County Oreg. Observed plants were cultivated for a period of 24 months in 2 liter containers. Certain phenotypical characteristics of the variety may vary under different environmental, cultural, agronomic, seasonal, and climatic conditions. Color references are made using The Royal Horticultural Society (London, England) Colour Chart, 2001, except where common terms of color are used.

For a comparison, several physical characteristics of the *clematis* variety 'Poulala' described and illustrated in U.S. Plant Pat. No. 10,990 are compared to 'Evipo049' in Chart 1.

CHART 1

| | 'Evipo049' | 'Poulala' |
|---|---|---|
| Flower diameter | 150 mm | 130 mm |
| Tepal upper surface after opening | White Group N155A with light intonations of Violet-Blue Group 92B. | Yellow Group 10D |
| Tepal count | 8 | 6 to 8 |

Flower and Flower Bud

Blooming habit: Continuous. The natural flowering period is generally from May to September.

Flower bud:
- *Size*.—Normally 55 mm in length. Bud diameter is 23 mm.
- *Bud form*.—Elliptic.
- *Texture*.—Pubescent.
- *Bud color*.—Yellow-Green Group 150D and Yellow-Green Group N144D.

Peduncle:
- *Surface texture*.—Pubescent.
- *Length*.—On average 80 mm.
- *Diameter*.—About 4 mm.
- *Color*.—Yellow-Green Group 144C.
- *Strength*.—Moderately strong.

Receptacle:
- *Surface texture*.—Pubescent.
- *Shape*.—Broad funnel.
- *Size*.—1 mm (h)×4 mm (w).
- *Color*.—Yellow-Green Group 144C.

Flower arrangement:
- *Location on vine*.—New and old growth.
- *Borne*.—In clusters of 3 to 7 flowers per flowering branch.

Flower bloom:
- *Size*.—On average, flowers are 150 mm in diameter and 30 mm in depth.
- *Profile*.—Open flowers are flat.
- *Fragrance*.—None.
- *Lasting quality*.—Flowers normally remain up to 10 days on the plant.

Tepals:
- *Tepal color*.—The upper surface is White Group N155A with light intonations of Violet-Blue Group 92B. The lower surface is White Group N155A with light intonations of Violet-Blue Group 92B. The lower surface has a central bar Yellow-White Group 158C.
- *Quantity*.—Normally 8 tepals.
- *Size*.—80 mm in length by 55 mm wide.
- *Shape*.—Individual tepal shape is ovate. The tepal apex is rounded. The tepal base acuminate.
- *Apex recurvature*.—None.
- *Tepal cross section*.—Flat.
- *Margins*.—Entire. Undulations absent.
- *Persistence*.—Tepals drop off cleanly.

Reproductive organs:
- *Arrangement*.—Open.
- *Pollen*.—None observed.
- *Anthers*.—Size: About 7 mm in length. Color: Greyed-Orange Group 176B. Quantity: On average, 45.
- *Filaments*.—Color: White Group 155B. Length: About 15 mm.
- *Pistils*.—Quantity: On average, 20.
- *Styles*.—Color: Yellow-White Group 145D. Length: About 15 mm.

Plant

Plant form: Climbing.

Plant growth: Moderately vigorous.

Size: Seasons growth attains about 100 cm in height. Average spread is 50 cm.

Stems:
- *Color*.—Juvenile stems are Yellow-Green Group 145B. Mature stems are Greyed-Red Group 178A.
- *Internodes*.—5 to 6 cm between nodes.
- *Length*.—Normally 30 cm from the base of the plant to the flowering portion of the stem.
- *Diameter*.—Normally 2 to 4 mm.
- *Texture*.—Mature stems are generally smooth.

Plant foliage:
- *Leaf characteristics*.—Deciduous.
- *Arrangement*.—Trifoliate.
- *Leaf size*.—Compound leaves are normally 170 mm (l)×130 mm (w). Leaflets are normally 55 mm (l)×45 mm (w).
- *Abundance*.—On average 2 leaves per 10 cm of stem.
- *Leaf color*.—Mature leaf color is Yellow-Green Group 144A above and Yellow-Green Group 146C underneath. Margins have intonations of Greyed-Purple Group 183B.
- *Stipules*.—Absent.
- *Petioles*.—Size: Normally 90 mm in length by about 2 mm diameter. Texture: Smooth. Color: Greyed-Purple Group 187A above, and Yellow-Green Group 145A underneath.
- *Petiolule*.—Size: Normally 15 mm in length by about 2 mm diameter. Texture: Smooth. Color: Greyed-Purple Group 187A above, and Yellow-Green Group 145A underneath.
- *Leaflet shape*.—Generally cordate. The apex is obtuse. The base is cordate to rounded.
- *Margin*.—Entire.
- *Surface*.—The upper side is smooth. The lower side is smooth.
- *Thickness*.—Average.
- *Glossiness*.—Not glossy.

Disease resistance: Subject to any disease that normally attacks the species. However the variety is more tolerant to *clematis* wilt, *Ascochyta clematidina*, than some *clematis* known to the inventors.

Cold hardiness: The variety is tolerant to USDA Hardiness Zone 6.

Heat tolerance: The variety has been found to be suitable for climate conditions found in the American Horticulture Society heat zone 7.

We claim:

1. A new and distinct variety of *clematis* plant named 'Evipo049', substantially as described and illustrated, due to its abundant near white flowers with good keepability, attractive long lasting foliage and compact growth, year round flowering under glasshouse conditions, suitability for production from softwood cuttings in pots, durable flowers and foliage which make the variety suitable for distribution in the floral industry.

* * * * *

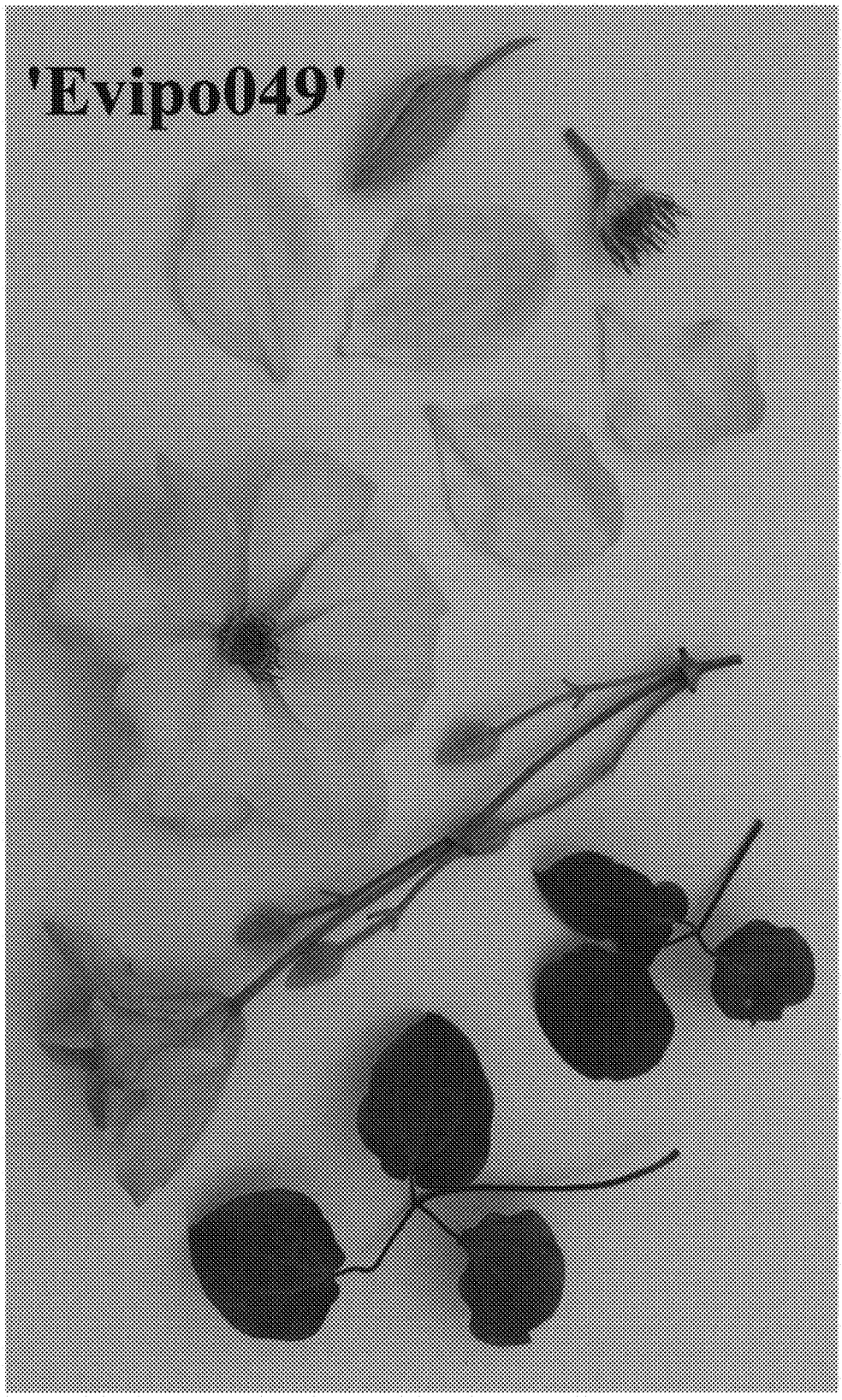
'Evipo049'